United States Patent [19]

Nelson

[11] Patent Number: 4,890,604

[45] Date of Patent: Jan. 2, 1990

[54] TRACTION ASSEMBLY

[76] Inventor: Dorand N. Nelson, 1074 Iowa St., St. Paul, Minn. 55117

[21] Appl. No.: 95,998

[22] Filed: Sep. 14, 1987

[51] Int. Cl.⁴ ........ A61F 5/04

[52] U.S. Cl. ........ 128/74; 128/71

[58] Field of Search ........ 128/71, 74, 69, 70, 128/48, 49, 50; 5/62

[56] References Cited

U.S. PATENT DOCUMENTS

| | | | |
|---|---|---|---|
| 2,243,013 | 5/1941 | Morey et al. | 128/52 |
| 2,433,548 | 12/1947 | Ecks | 128/49 |
| 2,658,754 | 11/1953 | Courtney | 5/60 |
| 3,060,925 | 10/1962 | Honsaker et al. | 128/71 |
| 3,081,085 | 3/1963 | Girolamo | 128/71 |
| 3,238,936 | 3/1966 | Siedentop | 128/71 |
| 3,293,667 | 12/1966 | Ohrberg | 5/62 |
| 3,343,531 | 9/1967 | Thompson | 128/69 |
| 3,441,014 | 4/1969 | Ramsey | 128/33 |
| 3,589,358 | 6/1971 | Megal | 128/71 |
| 3,638,646 | 2/1972 | Draux | 128/71 |
| 3,640,520 | 2/1972 | Wieland et al. | 5/62 |
| 3,741,200 | 6/1973 | Morm | 128/71 |
| 3,993,051 | 11/1976 | Maruyama | 128/70 |
| 4,006,499 | 2/1977 | Young | 5/62 |
| 4,144,880 | 3/1979 | Daniels | 128/74 |
| 4,194,499 | 3/1980 | Donnelly, Jr. | 5/62 |
| 4,379,450 | 4/1983 | Sjolinder | 128/74 |
| 4,452,439 | 6/1984 | Hogan | 5/62 |
| 4,531,731 | 7/1985 | Law | 128/71 |
| 4,638,516 | 1/1987 | Vrzalik | 5/62 |
| 4,672,697 | 6/1987 | Schurch | 128/71 |
| 4,726,358 | 2/1988 | Brady | 128/70 |

FOREIGN PATENT DOCUMENTS

| | | | |
|---|---|---|---|
| 1327131 | 4/1963 | France | 128/71 |
| 0858821 | 8/1981 | U.S.S.R. | 128/71 |

*Primary Examiner*—Edgar S. Burr
*Assistant Examiner*—Tonya Lamb
*Attorney, Agent, or Firm*—Burd, Bartz & Gutenkauf

[57] ABSTRACT

A traction assembly for placing a human body in traction under the inclined weight of the body for medical or therapeutic reasons. The major trunk portion of the body is supported on a movable platform. The body extremities, including the head and the ankles, are fixed relative to a frame. The platform is movable relative to the frame under the influence of gravity when the frame is placed at an inclination. The degree of traction placed on the body is dependent upon the weight of the body and the inclination of the frame with respect to a horizontal orientation. The frame can be reciprocated between first and second positions to place the body in gentle oscillating traction.

27 Claims, 3 Drawing Sheets

TRACTION ASSEMBLY

BACKGROUND OF THE INVENTION

Traction tables are used to apply tension to the human body for medical or therapeutic purposes, usually through application of tension force to the spinal column. This is often accomplished with equipment where the patient lies horizontally on a bed or table, and tension is applied through the application of weight at one or both extremities of the body, i.e., the head or the ankle region. While one extremity is restrained, for example, the head, force is applied to the other, as through a weight system, including straps connected to the ankles or feet at one end and trained over pulleys with downwardly depending weights at the other end. Such traction devices can be uncomfortable and dangerous. They do not readily admit of an oscillating-type application of gentle traction.

SUMMARY OF THE INVENTION

The invention pertains to a traction assembly in order to subject the human body to traction for medical or therapeutic purposes. The traction assembly includes a stationary stand supportable on a ground or floor surface and a table assembly connected to the stand. The table assembly includes a frame that is rotatably assembled to the stand for limited rotation about a horizontal axis. Power means can be provided, such as an electric or hydraulic motor to effect oscillatory movement of the frame with respect to the stand. A flat platform or table having a longitudinal dimension approximate that of a human trunk is slidably assembled to the frame for relatively friction-free, back-and-forth movement under gravitational influence in a longitudinal direction perpendicular to the axis of rotation of the frame.

Restraint means are connected to the frame and positioned for connection to the head and ankles or feet of a human body when positioned on the platform in order to restrain their movement relative to the frame. Upon rotation of the frame on the stand to incline the platform, the restraint means connected to the body extremity at the upward end of the inclination restrains the extremity relative to the frame, while the body trunk slides downwardly with the platform responsive to the weight of the body. The body is put in traction according to the weight of the body and the degree of inclination. As the inclination is increased, the downward component of the weight of the body is increased, and more traction is placed on the body. The frame can be oscillated back and forth, such that the body is moved gently in and out of a degree of traction. The traction applied to the body is safe and comfortable. The traction can be applied with either the head or the feet at the upper end of the inclination. In one form of the invention, the oscillation can be between first and second preselected, inclined positions. The amount of oscillation is adjustable.

IN THE DRAWINGS

DESCRIPTION OF PREFERRED EMBODIMENTS

Figure 1:
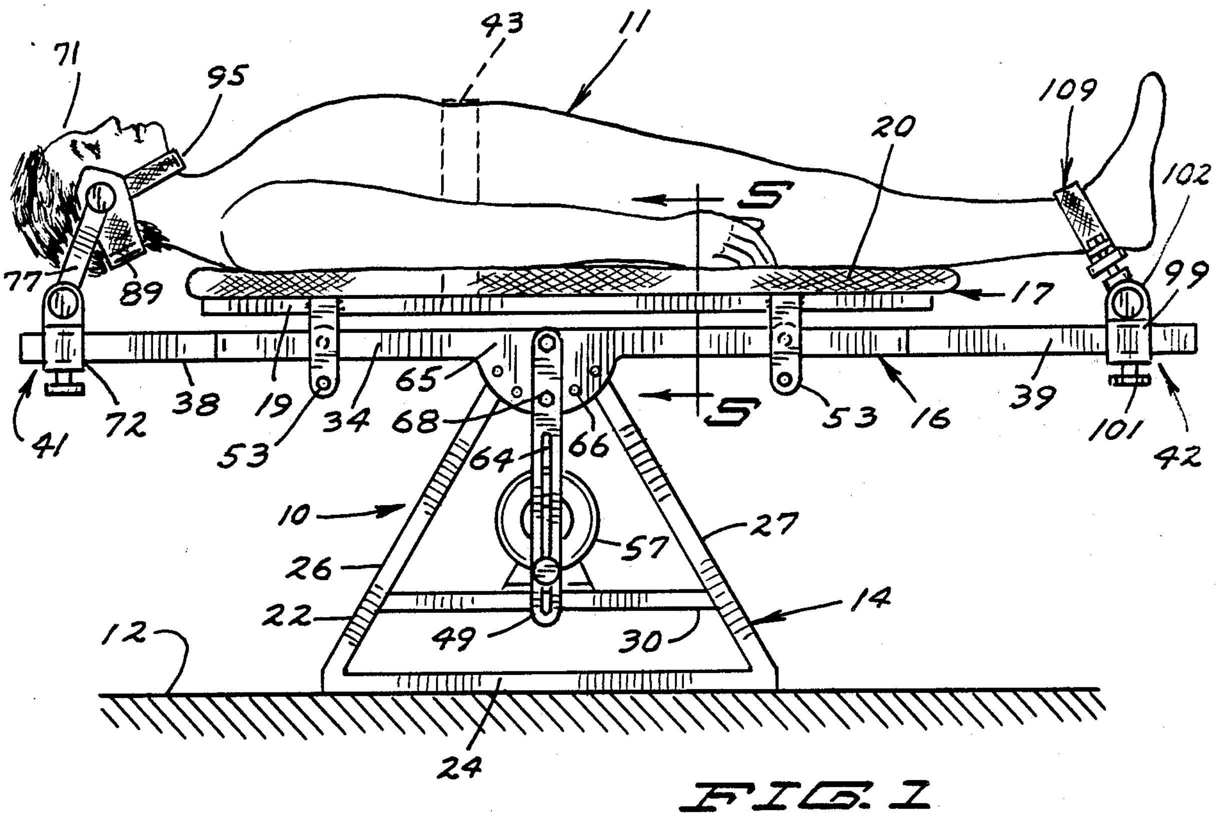
FIG. 1 is a side elevational view of a traction assembly according to one form of the invention having a human body supported thereon and in a horizontal orientation preparatory to applying traction.
Figure 2:
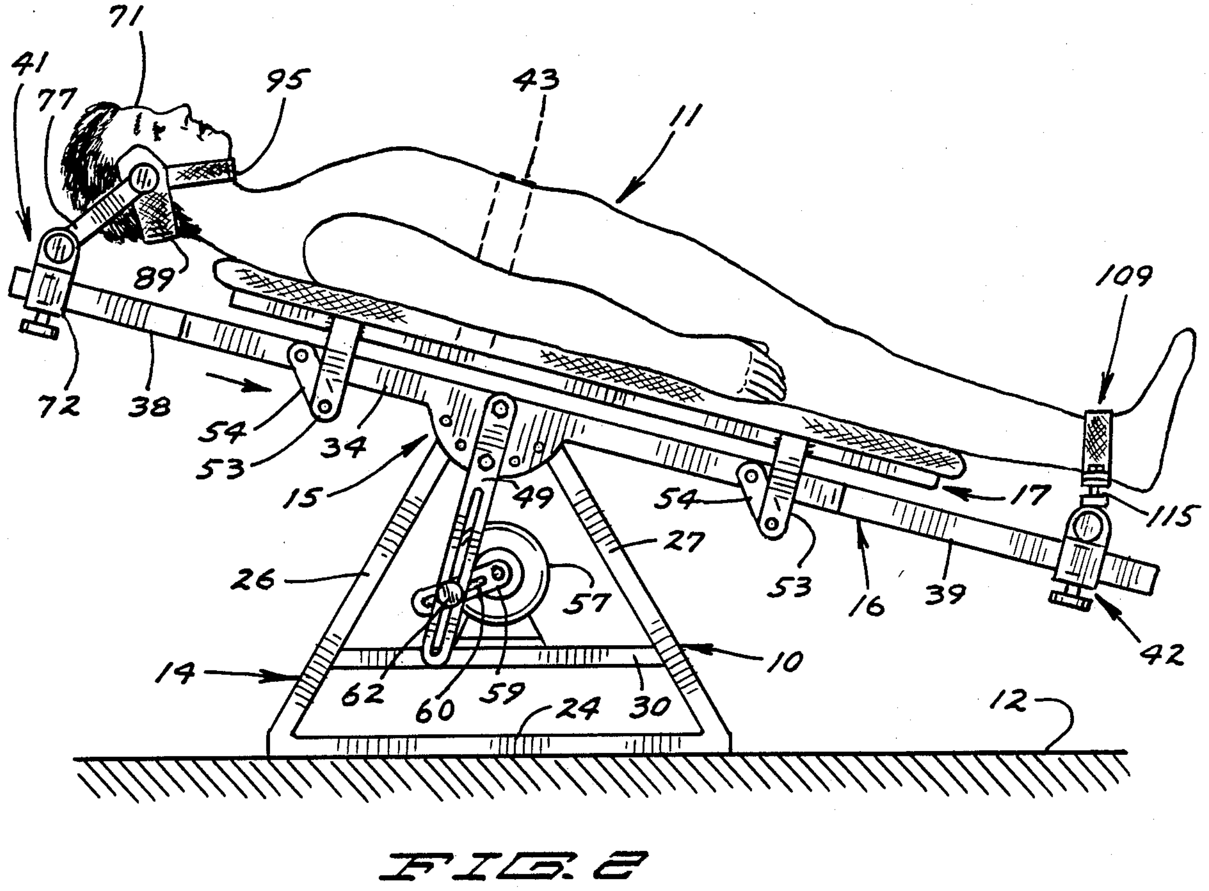
FIG. 2 is a side elevational view of the traction assembly of FIG. 1 with the table assembly inclined at an angle relative to a horizontal orientation so as to place the body in a measure of traction.
Figure 3:
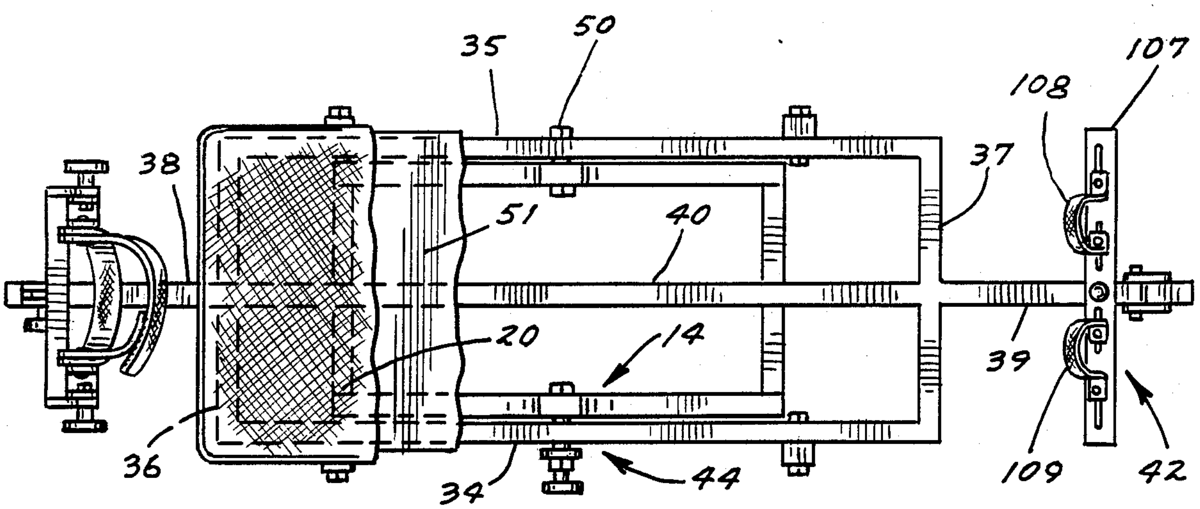
FIG. 3 is a top elevational view of the traction assembly of FIG. 1 partly fragmented and with the body removed for purposes of illustration.

Referring to FIGS. 1 through 3, there is shown a traction assembly 10 according to one form of the invention whereupon is positioned a body 11 for therapeutic or medical traction treatment. The traction assembly 10 is placed upon a floor 12 or such other suitable horizontal, flat surface. As shown in FIG. 1, a patient 11 is horizontally positioned on the traction assembly 10 preparatory to tilting of the table assembly. Upon tilting of the table assembly to an inclination, as shown in FIG. 2, the patient 11 is placed in traction. One extremity, or in the case of FIG. 2, the head is restrained relative to the frame portion of the table assembly. The lower body is placed in comfortable traction against the restraint of the head by movement with a sliding platform in the downward direction under the influence of gravity. The body can be placed in static traction, or it can be oscillated back and forth between first and second inclined positions, or between a horizontal and an inclined position according to the desirable or prescribed mode of treatment.

The traction assembly indicated generally at 10 includes a stand 14 positioned with respect to the floor 12 carrying a table assembly 15 mounted for rotation on the stand 14. Table assembly 15 includes a support frame 16 and a patient platform 17 slidably assembled to the support frame 16 for linear back-and-forth longitudinal movement parallel to the frame 16 under the influence of gravity. The patient support platform 17 includes a table structure 19 and a patient pad 20 placed on top of the table structure 19 in position to support the major trunk and upper leg portions of a patient 11.

Figure 4:
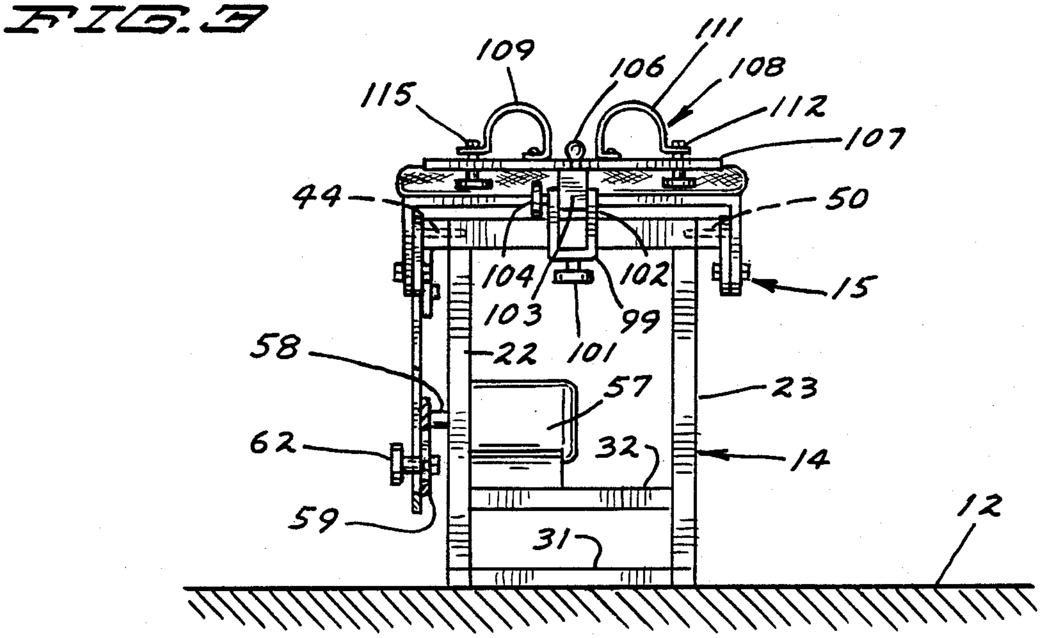
FIG. 4 is an end plan view of the traction assembly of FIG. 3.

Stand 14 includes parallel, triangularly shaped legs 22, 23 (FIG. 4). Each leg has a horizontal lower member 24 and upwardly convergent side members 26, 27 joined at an apex 29. An intermediate horizontal brace 30 connects intermediate portions of the leg members 26, 27. Legs, 22, 23 are connected by a lower lateral brace 31 (see FIG. 4) and an intermediate lateral brace 32 disposed between the intermediate longitudinal braces 30.

Frame 16 includes a generally rectangular mid-portion comprised of longitudinal side rails 34, 35 connected by lateral forward and rearward end rails 36, 37. A center rail 40 extends between the lateral end rails 36, 37. A forward extension of the center rail 40 is comprised as a forward tongue 38, and a rearward extension is comprised as a rearward tongue 39. A head restraint assembly 41 is adjustably fixed on the forward tongue 38. A foot restraint assembly 42 is adjustably mounted on the rearward tongue 39.

Figure 5:
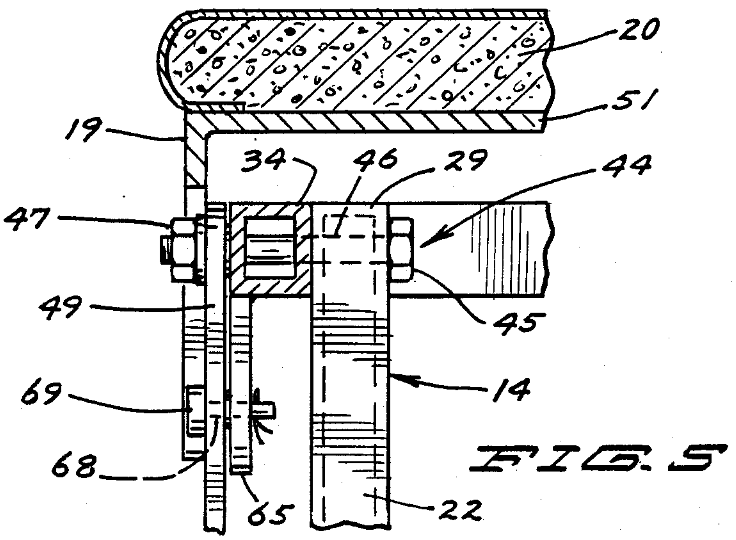
FIG. 5 is an enlarged sectional view of a portion of the traction assembly of FIG. 1 taken along line 5—5 thereof.

Frame 16 is pivotally connected to stand 14 for rotation about a fixed lateral, horizontal axis. As shown in FIG. 5, a pivot pin assembly 44 connects the side rail 34 of frame 16 to the apex 29 of leg 22 of stand 14. Pivot pin assembly 44 includes a head 45 disposed adjacent the inside surface of the stand 14 and connected to a shank 46. Shank 46 passes through suitable pivot openings located in the apex 29 of leg 22, in the side rail 34 and through a drive link 49. A lock nut 47 is located on the opposite end of the shank 46, whereby a pivotal connection is formed about a horizontal axis coincidental with the axis of shank 46 between the leg 22 of stand 14 and the side rail 34 of the frame 16. A corresponding pivot pin assembly 50 connects the opposite leg 23 to the opposite side rail 35 of frame 16 for pivotal rotation about a coincidental axis, the pivot pin assembly 50 being the same construction as the first pivot pin assembly 44.

Patient platform 17 is slidably connected to or suspended by frame 16 for parallel longitudinal movement with respect to it under the influence of gravity when the frame 16 is inclined. Table 19 of platform 17 has a flat table top 51, which is disposed parallel to and located above the plane of frame 16 and supports patient pad 20. Arms 53 are rigidly connected to and extend downward from side edges of the table top 51 near the corners thereof. Two of the arms 53 extend downwardly from each side on opposite sides of the pivot axis of the frame 16. The lower ends of the arms extend below the frame 16 and are pivotally connected to the lower ends of suspension members or pivot links 54. The upper ends of the pivot links 54 are pivotally connected to side rails of the frame 16. The pivot axes of the links and arms are parallel to the pivotal axis of the frame with respect to the stand. The table 19 is suspended by and swings about the pivot links 54 upon rotation of the frame 16. In movement from a horizontal orientation like that of FIG. 1 to an inclined position like that of FIG. 2, the major component of the swinging movement of the table relative to the frame is longitudinal in a direction parallel to the plane of the frame.

Oscillating or reciprocating movement of the frame 16 with respect to the stand 14 is effected by a suitable power means shown as an electric motor 57 mounted on the longitudinal and lateral braces 30, 32 of stand 14. Motor 57 has a horizontal output shaft 58 parallel to the axis of rotation of the frame 16 relative to the stand 14. Output shaft 58 of motor 57 is connected to a radiating arm or crank 59 having a crank slot 60 carrying an adjustable crank pin 62 (FIG. 4). The end of crank pin 62 is releasably secured with respect to the slot 60, as by having lock nuts secured on the shank of crank pin 62 on opposite sides of the slot 60. Drive link 49 has an elongate lost motion slot 64. The shank of crank pin 62 adjacent the head is slidably accommodated in the slot 64 and readily movable therein along the length of the slot.

The upper end of drive link 49 is interconnected with the pivot pin assembly 44. A portion of the drive link 49 just beneath the pivot pin assembly 44 faces an index plate 65 that is fastened to and extended downwardly from the side rail 34 of frame 16. The index plate 65 has an arcuate pattern of index holes 66 arcuately disposed about the pivot axis of frame 16. Drive link 49 has an index opening 68 that can be aligned with a selected index hole 66. A locking pin 69 (FIG. 5) passes through the index opening 68 and drive link 49 and through one of the index holes 66 in index plate 65 whereby the index plate 65, side rail 34 and frame 16 are locked for corresponding movement with the drive link 49.

Oscillating movement of the drive link 49 translates into oscillating movement of the frame 16. Upon rotation of drive shaft 58 of motor 57, the drive link 49 is moved back and forth by the crank pin 62 as it rides up and down in the drive link slot 64. As shown in FIGS. 1 and 2, the drive shaft 58 rotates clockwise, as viewed therein, to move the frame 16 from a horizontal position in FIG. 1 to an inclined position in FIG. 2, while the crank pin 62 moves the power link 49 to one side as it moves upward of the slot 64. Upon completion of one rotation, the frame 16 will have moved between an inclination, as shown in FIG. 2, to the opposite inclination and back to the starting position of FIG. 1.

The purpose of the index holes 66 on the index plate 65 is to set a starting position or inclination of oscillation. In FIG. 1, the starting position of oscillation is a horizontal position. However, the lock pin 69 can be removed and the table rotated to a position where the index opening of the drive link 49 faces another index hole 66, which will position the table at inclination when the motor 57 and drive link 49 are at the starting position shown in FIG. 1. The table oscillation will then begin with this inclination as a starting or "zero" point and oscillate an equal angular amount in either direction from that starting point. Adjustment of the crank pin 62 in the crank arm slot 60 is effective to regulate the degree of oscillation or the angle of rotation through which the table assembly 15 rotates. Motor 57 can be variable speed so as to regulate the speed of oscillation.

Figure 6:
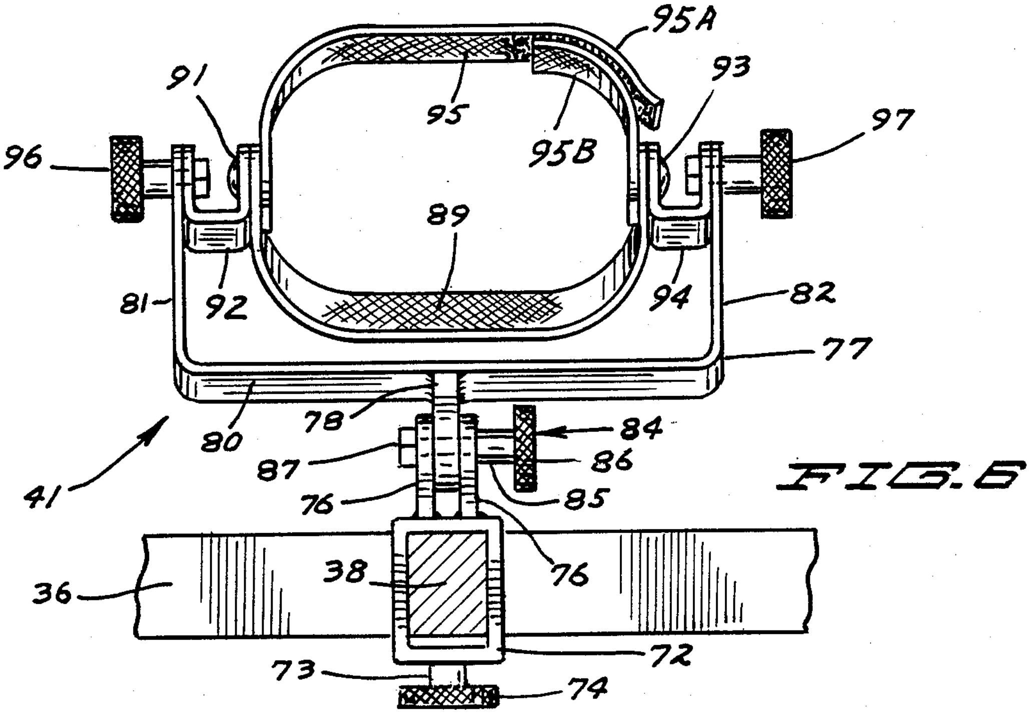
FIG. 6 is an enlarged view of the head restraint mechanism of the traction assembly of FIG. 1 as viewed from a longitudinal end.

The head 71 of patient 11 is secured with respect to support frame 16 by head restraint assembly 41, which is adjustably mounted on tongue 38. Referring to FIGS. 1 and 6, a rectangular, tubular clamp block 72 engages the forward tongue 38 and is slidable for adjustment of position. A set screw 73 turned by a head 74 is positioned on the bottom portion of the clamp block 72 to fix the position thereof with respect to the forward tongue 38. A pair of upstanding mounting ears 76 are disposed on the upper surface of clamp block 72. A Y-shaped yoke 77 has a stem 78 connected centrally to a base member 80, and parallel arms 81, 82 extended upwardly from the outer ends of the base member 80. The stem 78 is disposed between the mounting ears 76 and is angularly adjustable therein. A screw lock assembly 84 includes a shank 85 rotated by a head 86 and having a reduced diameter portion that passes through suitable openings provided in the mounting ears 76 and the stem 78. A nut 87 locks the relative angular position of the stem 78 relative to the mounting ears 76.

A head sling 89 fills yoke 77 and is secured in opposite ends to inside rivet assemblies 91, 93 located at the inner ends of U-shaped support members 92, 94. U-shaped support members 92, 94 are connected for angular adjustment to the upper ends of yoke legs 81, 82 by releasable bolt-lock assemblies 96, 97. A chin strap 95 is also fastened at its ends by rivet assemblies 91, 93 to the inner ends of the support members 92, 94. As shown in FIGS. 1 and 2, the lower rear portion of the patient's head is comfortably situated in the head sling 89 while the chin strap 95 extends around the lower chin portion to hold the patient's head secure. Chin strap connecting ends 95A, 95B are releasably connected by facing sections of synthetic material of the type that adheres when pressed together, such as Velcro material.

A foot restraint assembly 42, as shown in FIGS. 1 and 4, includes a rectangular, tubular clamp block 99 slidably accommodated on rear tongue 39 inadjustable relationship and securable in conventional fashion by a set screw 101 threaded in the bottom surface thereof for contact with the bottom surface of the tongue 39. Loosening of the set screw 101 permits back-and-forth adjustment of the clamp block 99. A pair of fingers or ears 102 extend upwardly from the top surface of clamp block 99 and straddle a mounting block 103. A lock screw 104 secures the mounting block 103 to the ears 102.

A spindle or ball mount 106 located on the top of the mounting block 103 passes through a central opening in a horizontal crosspiece 107 which carries first and second ankle cuff assemblies 108, 109. Cuff assembly 108 includes a strap 111 having an interior end fixed to the cross member 107 and a free end extendible around the person's ankle and fixable by a releasable clamp assembly 112. The other cuff assembly 109 has a strap 119 fixed at an interior end to the cross member 107 with a free end extendible around the other ankle to a second releasable clamp assembly 115.

In use of the traction table 10, the head and ankle restraint assemblies 41, 42 are adjusted on the tongues 38, 39 according to the stature of the individual on the pad 20 of table assembly 15, who is in a horizontal orientation preparatory to the application of traction. The individual's head 71 is placed in the head restraint assembly with the lower rear portion of the head rested in the sling 89, and the chin strap 95 crossing underneath the chin. The right and left ankles are inserted in the cuff assemblies 108, 109, which cross over the upper portions of the ankles, with the lower ankle portions being rested on the cross member 107. The ankle and feet of the person are thus restrained, as well as the head, with respect to movement relative to the frame 16. A conventional body strap indicated at 43 in FIGS. 1 and 2 can be applied to the individual to secure him relatively to the pad 20.

The platform 17 is movable with respect to the frame 16 upon movement of the frame 16 away from the horizontal orientation. The individual 11 is placed in traction by tilting the frame 16, for example, as shown in FIG. 2. The patient platform 17 moves with respect to the frame 16 in a linear direction parallel to it under the influence of the weight of the individual. For example, the individual's head 71 is restrained in FIG. 2, and the patient platform 17 moves from left to right along the inclination of the frame 16 under the influence of gravity and the weight of the person. This places the person in traction an amount according to the amount of inclination and the weight of the person. This is a comfortable amount of traction which can readily be withstood by the patient and is disturbed over the body length of the patient.

The patient can be left in static rotation or the platform assembly can be oscillated between first and second positions. The degree of oscillation is adjusted by adjustment of the crank pin 62 relative to the crank arm 59 on the motor 57. The speed of oscillation is governed by the speed of motor 57. The starting point, or midpoint, of the back-and-forth oscillation is governed by adjustment of the drive link 49 on the index plate 65. Traction can be applied with the head located beneath the feet or, as shown, the feet located beneath the head, or an oscillation between the two. In either case, the patient platform assembly 17 moves freely in a direction parallel to the frame 16, with the extremities of the patient restrained, thus inducing traction in the patient according to the inclination and the patient weight.

Figure 7:
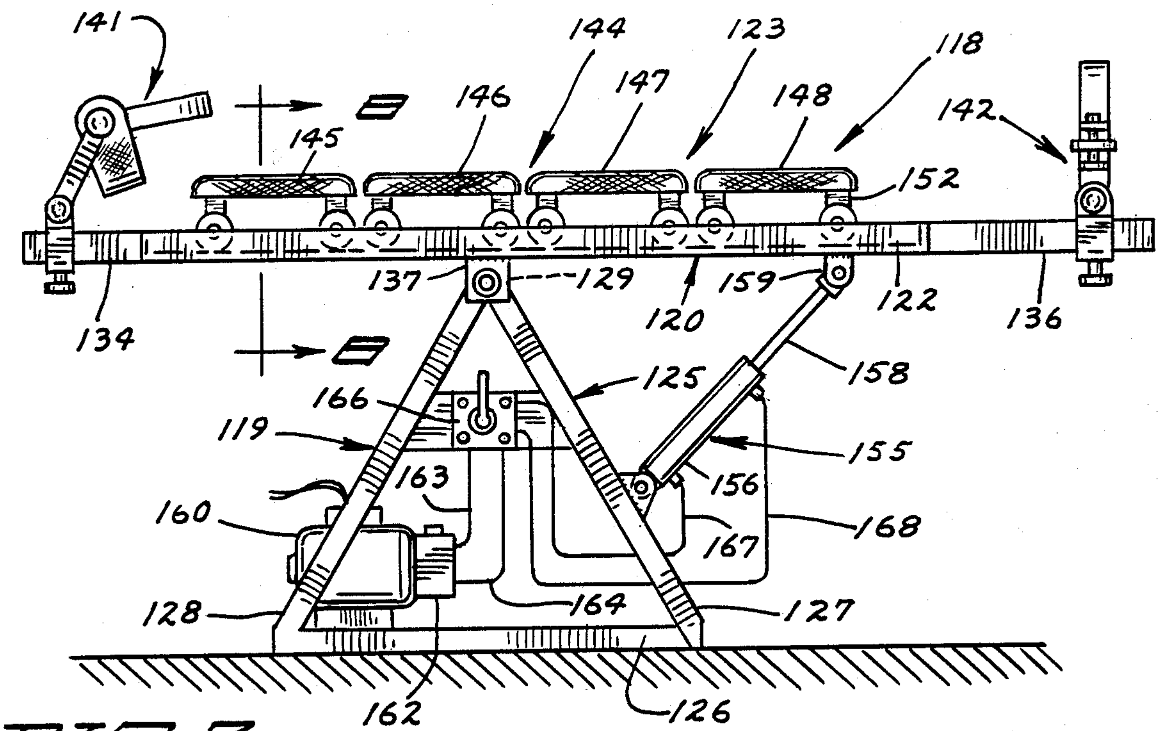
FIG. 7 is a side elevational view of a traction assembly according to another form of the invention.
Figure 8:
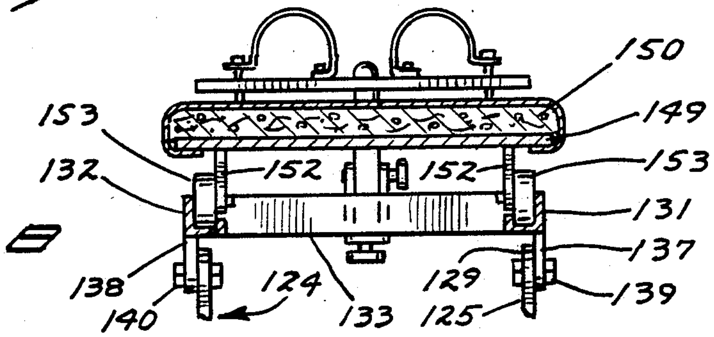
FIG. 8 is an enlarged sectional view of a portion of the traction assembly of FIG. 7 taken along the line 8—8 thereof.

Referring to FIGS. 7 and 8, there is shown a traction assembly according to another form of the invention indicated generally at 118, including a stand 119 and a table assembly 120 mounted for rotation relative to the stand 119. Table assembly 120 includes a support frame 122 and a patient platform assembly 123 assembled to the support frame 122 for linear back-and-forth parallel, longitudinal movement with respect to the frame 122 under the influence of gravity.

Stand 119 includes a pair of triangularly shaped legs 124, 125. As shown in FIG. 7, the leg 125 includes a base member 126 and upwardly convergent side members 127, 128, which converge at an apex 129. The opposite leg 124 is symmetrical in construction.

Frame 122 includes side rails 131 and 132, which are J-shaped or channel-shaped having an interior edge shorter than the exterior edge, as shown in FIG. 8, forming a longitudinal track. A forward end rail joins the forward ends of the side rails 131, 132. Forward tongue 134 extends forwardly from the end rail. A rearward end rail 133 connects the rearward ends of the side rails 131, 132, and a rearward tongue 136 extends longitudinally and centrally from the rearward end rail.

A pair of pivot plates 137, 138 are centrally fastened to the respective side rails 131, 132 and extend downwardly, as shown in FIG. 8. A pivot pin assembly 139 pivotally connects the first pivot plate 137 to the apex 129 of the right leg 125. In like fashion, another pivot pin assembly 140 pivotally connects the apex of leg 124 to the second pivot plate 138 in coaxial relationship to the pivotal connection of the first pivot assembly 139. Frame 132 pivots on the stand 119 about a fixed horizontal axis for back-and-forth inclination of the table assembly 120.

A head restraint assembly 141 is movably assembled on the forward tongue 134. A foot and ankle restraint assembly 142 if movably assembled to the rearward tongue 136. The head and foot restraint assemblies are identical in construction to those described earlier with respect to the head restraint assembly 41 and the foot restraint assembly 42 and move in like fashion on the forward and rearward tongues of the frame 122.

Platform assembly 123 includes a wheeled carriage 144 riding on the track of frame 122 formed by the channel-shaped side rails 131, 132. A carriage is comprised of a plurality of wheeled trolley units 145–148 interconnected by suitable means. Each trolley unit has a flat top member 149 covered by a pad or cushion 150 (see FIG. 8). Each trolley unit has four depending legs 152, each leg carrying a roller or wheel 153 engaged in the channel or track of the rails 131, 132. Patient carrier 144, under the influence of gravity, is easily movable back and forth on the side rails 131, 132.

Power means for reciprocal movement of the table assembly 120 includes a hydraulic power assembly having a hydraulic actuator 155 of the double-acting cylinder-piston variety with a cylinder 156 pivotally connected to a stand leg member 127, and a rod 158 reciprocally movable with respect to the cylinder 156 and pivotally connected at its outer end 159 to the frame 122 at a location longitudinally spaced from the axis of rotation of frame 122 with respect to the stand 119. Hydraulic pump 160 mounted on the stand 119 and hydraulic reservoir 162 provide and receive hydraulic fluid through hydraulic lines 163, 164 to the hydraulic control panel 166, which selectively delivers and receives hydraulic fluid from the input and output ends of the cylinder 156 through hydraulic lines 167, 168.

The control panel 166 can be manual or automatic as is conventionally known to operate the hydraulic actuator 155 to tilt the table 120 with respect to the stand 119 at a selected inclination. The actuator 155 can hold the table assembly 120 at a selected inclination for static traction or can reciprocate between first and second positions of the table assembly and provide an oscillating traction motion.

In use, the trunk portion of the patient is positioned on the carriage 144, with the head and feet restrained by the restraint assemblies 141, 142. A body strap can be used if necessary or desirable. The table is placed at an inclination such that the carriage 144 moves longitudinally with respect to the track of frame 122 in a downward direction so as to place the patient in traction under the influence of the patient's own weight, the degree of traction being dependent upon the angle of inclination and the weight of the patient. The traction can be static or the assembly can gently oscillate between first and second positions which can be between a horizontal and an inclined position or between one inclined position and another. The traction is easily adjustable to the patient tolerance.

While there have been shown and described certain embodiments of the invention, it will be apparent that deviations and modifications can be had without departing from the scope and spirit of the invention.

The embodiments of the invention in which exclusive property or privilege is claimed are defined as follows:

1. A patient traction assembly comprising:

a stand for support with respect to a ground surface;

a table assembly including a frame having a first end and a second end longitudinally spaced from the first end and a single flat platform having a first end and a second end longitudinally spaced from and fixed relative to the first end of the frame;

means rotatably connecting the frame to the stand for rotational movement of the frame with respect to the stand about a horizontal axis perpendicular to the longitudinal dimension of the frame, the frame being fixed longitudinally with respect to the axis of rotation;

said flat platform having a length sufficient to support the trunk portion of a patient between the first and second platform ends from approximately the shoulder area to the mid-leg area in a longitudinal orientation perpendicular to the horizontal axis of rotation of the frame;

means movably connecting the platform to the frame permitting longitudinal movement of the platform between the first and second ends of the frame under the influence of gravity with respect to the frame in a direction perpendicular to the horizontal axis of rotation of the frame when the platform is angularly disposed with respect to a horizontal orientation; and patient restraint means connected to the frame and connectable to a patient extremity when the patient trunk is positioned on the platform, including a head restraint assembly fixed with respect to the frame proximate the first end of the platform and comprising a part of the first end of the frame, and an ankle restraint assembly fixed with respect to the frame proximate the second end of the platform and comprising a part of the second end of the frame whereby traction is applied to the trunk of the patient between the head and the ankles upon rotation of the frame to an inclined position of the frame by downward gravitational movement of the platform with respect to the frame and with respect to a restrained patient extremity.

2. The patient traction assembly of claim 1 including: power means for reciprocal rotation of the frame with respect to the stand.

3. The patient traction assembly of claim 2 wherein: said power means comprises an electric motor.

4. The patient traction assembly of claim 2 wherein: said power means comprises a hydraulic power assembly.

5. The patient traction assembly of claim 1 including: means for longitudinally adjusting the position of the head and ankle restraint assemblies with respect to the platform.

6. The patient traction assembly of claim 1 wherein: said head restraint assembly includes a Y-shaped yoke, a head sling supported in said yoke to support the lower rear portions of a head, and a chin strap supported in said yoke extendible around the chin of a patient.

7. The patient traction assembly of claim 6 wherein: said frame has a forwardly extended tongue, said head restraint assembly being movably adjustable on the forwardly extended tongue.

8. The patient traction assembly of claim 6 wherein: said ankle restraint assembly includes first and second ankle straps extendible around the ankles of a patient.

9. The traction assembly of claim 8 including: power means for reciprocal rotation of the frame on the stand.

10. The traction assembly of claim 1 wherein: said frame includes a pair of longitudinal frame members; said platform includes a table situated above the frame and having legs depending to a position below the frame and straddling the sides of the frame, said means movably connecting the platform to the frame including pivot links pivotally connected at one end to the lower ends of the legs of the table and at the other ends to the longitudinal frame members.

11. The traction assembly of claim 10 including: power means comprised as an electric motor connected to the frame and the stand for reciprocal rotation of the frame with respect to the stand.

12. The traction assembly of claim 11 wherein: said electric motor has a drive shaft attached to a crank rod; said crank rod being assembled to one end of a drive link having an elongate drive link slot by a crank pin having a shank ridable in the drive link slot; the opposite end of the drive link being connected to the platform in spaced relationship to the horizontal axis of rotation of the platform.

13. The traction assembly of claim 12 including: index means connected between the drive link and the frame to adjust the starting position of rotation of the frame with respect to a horizontal orientation.

14. The traction assembly of claim 1 wherein: said means rotatably connecting the frame to the stand includes pivotal means connecting the frame to the stand intermediate the frame ends for pivotal movement of the frame about a fixed horizontal axis.

15. The traction assembly of claim 14 including: power means for reciprocating movement of the frame with respect to the stand, said power means having reciprocating means, a drive link connected at a first end to the reciprocating means and at the second end to the frame for reciprocal movement of the frame upon operation of the power means.

16. The traction assembly of claim 15 including: an index plate connected to a side of the frame and having a plurality of index stations connectable to the second end of the drive link to adjust the angular starting position of reciprocation of the frame.

17. The traction assembly of claim 16 wherein: said index plate has a plurality of index holes arranged in an arcuate pattern about the axis of rotation of the frame, the second end of the drive link having an index opening interconnectable with a selected index hole on the index plate to adjust the starting position of reciprocation of the frame.

18. The traction assembly of claim 17 wherein: said power means is an electric motor having an output shaft, said reciprocating means including said output shaft connected to a crank arm, said crank arm connected to the first end of the drive link, said first end of the drive link having an elongate slot, a crank pin connected to the crank arm and having a shank riding in the slot of the drive link operable to move the first end of the drive link back and forth upon reciprocation of the crank arm with the electric motor.

19. The traction assembly of claim 18 wherein: said platform has a plurality of downwardly depending arms in straddling relationship to the frame, a plurality of pivot links connected at one end to the lower ends of the arms and at the opposite end to the frame to permit sliding movement of the platform with respect to the frame upon inclination of the frame.

20. A traction assembly comprising:

frame means having a first end including head restraint means and a second end including ankle restraint means fixed with respect to the head restraint means;

single platform having first and second ends and a generally flat surface and a sufficient length for support of the trunk portion of a patient between the lower neck and mid-leg region;

connecting means connecting the frame means to the platform with the first end of the platform located proximate the head restraint means and the second end of the platform located proximate the ankle restraint means and permitting longitudinal movement of the platform with respect to the first end and the second end of the frame means under the influence of gravity;

said head and ankle restraint means fixedly connected to the frame means and connectable to patient extremities to secure the extremities of the patient from movement with respect to the frame means;

support means to supply rotational support to the frame means including rotational axis means to move the frame means between horizontal and inclined positions, the frame being fixed longitudinally with respect to the rotational axis means.

21. The traction assembly of claim 20 wherein: the connecting means is comprised as a plurality of suspension members pivotally connected between the platform and the frame means.

22. The traction assembly of claim 20 wherein: said connecting means comprises a roller and track assembly.

23. The traction assembly of claim 22 wherein: said roller and track assembly includes parallel members of said frame means forming a track, and roller means on the platform engaging the track of the frame means.

24. The traction assembly of claim 23 wherein: said platform includes a wheeled carriage having said roller means.

25. The traction assembly of claim 20 wherein: said platform includes a carriage supported on wheels; said connecting means including longitudinal tracks of the frame means to support the wheeled carriage and permit the carriage to roll back and forth on the track under the influence of gravity.

26. The traction assembly of claim 20 wherein: said connecting means includes a plurality of pivot links pivotally connected at one end to the frame means and at the other end to the platform suspending the platform from the frame means.

27. The traction assembly of claim 26 wherein: said platform has a plurality of downwardly depending legs extending to a location beneath the frame means, said pivot links being connected to the bottom ends of the legs extending from the platform.

* * * * *